US006114557A

United States Patent [19]
Uhlenbrock et al.

[11] Patent Number: 6,114,557
[45] Date of Patent: *Sep. 5, 2000

[54] METHODS FOR PREPARING RUTHENIUM AND OSMIUM COMPOUNDS

[75] Inventors: Stefan Uhlenbrock, Boise; Brian A. Vaartstra, Nampa, both of Id.

[73] Assignee: Micron Technology, Inc., Boise, Id.

[*] Notice: This patent is subject to a terminal disclaimer.

[21] Appl. No.: 09/372,427

[22] Filed: Aug. 11, 1999

Related U.S. Application Data

[63] Continuation of application No. 09/141,431, Aug. 27, 1998.
[51] Int. Cl.$^7$ .............................. C07F 15/00; C07F 9/02
[52] U.S. Cl. .............................. 556/21; 556/28; 556/136; 556/137; 427/248.1
[58] Field of Search .............................. 556/21, 28, 136, 556/137; 427/248.1

[56] References Cited

U.S. PATENT DOCUMENTS

| 5,130,172 | 7/1992 | Hicks et al. | 427/252 |
| 5,314,727 | 5/1994 | McCormick et al. | 427/584 |
| 5,352,488 | 10/1994 | Spencer et al. | 427/250 |
| 5,372,849 | 12/1994 | McCormick et al. | 427/253 |
| 5,392,189 | 2/1995 | Fazan et al. | 361/305 |
| 5,510,651 | 4/1996 | Maniar et al. | 257/751 |
| 5,520,996 | 5/1996 | Douglas et al. | 428/209 |
| 5,555,486 | 9/1996 | Kingon et al. | 361/305 |
| 5,561,307 | 10/1996 | Mihara et al. | 257/295 |
| 5,566,045 | 10/1996 | Summerfelt et al. | 361/321.1 |
| 5,581,436 | 12/1996 | Summerfelt et al. | 361/321.1 |

OTHER PUBLICATIONS

Anderson et al., Organometallics, vol. 14, pp. 3516–3526, 1995.
Bennett et al., J. Chem. Soc. D., (7), pp. 341–342, 1971.
Burt et al., "Hydrocarbon Complexes of Ruthenium. Part III. Reactions of Cycloheptatrienes with Ruthenium Carbonyl", *J.C.S. Dalton Trans.*, 8, 731–736 (1975).
Chatzitheodorou et al., "Low Temperature Chemical Preparation of Semiconducting Transition Metal Chalcogenide Films for Energy Conversion and Storage, Lubrication, and Surface Protection", *Mater. Res. Bull.*, Abstract No. 109:233267b, 1 pg. (Dec. 1988).
Deganello, "The Reaction of cis–Bicyclo[6.2.0]DECA–2,4, 6–TRIENE with Dodecacarbonyltriruthenium", *90*, C31–C33 (1975).
Edwards et al., "The photochemical generation of novel neutral mononuclear ruthenium complexes and their reactivity", *J. Organ. Chem.*, 503, 15–20 (1995).
Ferrari et al., "Reactions of Dodecacarbonyltriosmium with Dienic Ligands", *J. Organ. Chem.*, 182, 245–249 (1979).
Schumann et al., "Tricarbonylbis(Tri–t–Butylphosphin)Eisen(0) Und–Ruthenium(0)", *J. Organ. Chem.*, 166, 233–239 (1979).

Siegl et al., "Ruthenium(0) and Ruthenium (II) Complexes with 1,1,1–Tris(diphenylphosphinomethyl)ethane", *Inorganic Chemistry*, 12, 674–677 (1973).
Sosinsky et al., "Hydrocarbon Complexes of Ruthenium. Part IV. Cyclic Dienyl Complexes", *J.C.S. Dalton Trans.*, 16–17, 1633–1640 (1975).
Whitesides et al., "Cleavage of Carbon–Carbon Sigma Bonds by $Ru_3(CO)_{12}$", *J. Chem. Soc., Chem. Commun.*, 3, 87 (1973).
Anderson et al., "Carborane Complexes of Ruthenium: A Convenient Synthesis of $[Ru(CO)_3(\eta^5-7,8-C_2B_9H_{11}]$ and a Study of Reactions of This Complex," *Organometallics*, 14, 3516–3526 (1995).
Bennett et al., "Mono–olefin Chelate Complexes of Iron (0) and Ruthenium(0) with an Olefinic Tertiary Phosphine," *J. Chem. Soc. D.*, 7, 341–342 (1971).
Cowles et al., "Relative Reactivity of Co–ordinated Ligands in the Dienyltricarbonyl–ruthenium Cation, [(dienyl) $Ru(CO)_3]^+$," *Chem. Commun.*, 392 (Feb., 1969).
Green et al., "Chemical Vapor Deposition of Ruthenium and Ruthenium Dioxide Films," *J. Electrochem. Soc.*, 132, 2677–2685 (1985).
Johnson et al., "Chemistry," *Nature*, 901–902 (Mar. 1967).
Liao et al., "Characterization of $RuO_2$ thin films deposited on Si by metal–organic chemical vapor deposition," *Thin Solid Films*, 287, 74–79 (1996).
Macchioni et al., "Cationic Bis–and Tris($\eta^2$–(pyrazol–1–yl)methane) Acetyl Complexes of Iron (II) and Ruthenium (II): Synthesis, Characterization, Reactivity, and Interionic Solution Structure by NOESY NMR Spectroscopy," *Organometallics*, 16, 2139–2145 (1997).
Senzaki et al., *Proc. Electrochem. Soc.*, 97(25), 933–943 (Chemical Abstract 128:264103). (1997).
Shin, "Characterization of $RuO_2$ Thin Films Prepared by Hot–Wall Metallorganic Chemical Vapor Deposition," *J. Electrochem. Soc.*, 144, 1055 (1997).
Versteeg et al., "Metalorganic Chemical Vapor Deposition By Pulsed Liquid Injection Using An Ultrasonic Nozzle: Titanium Dioxide on Sapphire from Titanium (IV) Isopropoxide," *Journal of the American Ceramic Society*, 78, 2763–2768 (1995).
Yuan, "Low–Temperature Chemical Vapor Deposition of Ruthenium Dioxide form Ruthenium Tetroxide: A Simple Approach to High–Purity $RuO_2$ Films," *Chem. Mater.*, 5, 908 (1993).

*Primary Examiner*—Porfirio Nazario-Gonzalez
*Attorney, Agent, or Firm*—Mueting, Raasch & Gebhardt, P.A.

[57] ABSTRACT

The present invention provides methods for the preparation of compounds of the formula (Formula I):

$$L_yM(CO)_z$$

wherein M is Ru or Os, each L is independently a neutral ligand, y=1–4, and z=1–5. These methods involve the reaction of $Ru_3(CO)_{12}$ or $Os_3(CO)_{12}$ with a neutral ligand in a solvent system having a boiling point higher than that of benzene at atmospheric pressure.

20 Claims, No Drawings

METHODS FOR PREPARING RUTHENIUM AND OSMIUM COMPOUNDS

This is a continuation of application Ser. No. 09/141,431, filed Aug. 27, 1998, (pending), which is incorporated herein by reference.

FIELD OF THE INVENTION

This invention relates to the preparation of ruthenium and osmium compounds, which are particularly useful as chemical vapor deposition precursors.

BACKGROUND OF THE INVENTION

Films of metals and metal oxides, particularly ruthenium and osmium films and oxides thereof, are becoming important for a variety of electronic and electrochemical applications. For example, high quality $RuO_2$ thin films deposited on silicon wafers have recently gained interest for use in ferroelectric memories. Ruthenium and osmium films are generally unreactive to silicon and metal oxides, resistant to diffusion of oxygen and silicon, and are good conductors. Oxides of these metals also possess these properties, although perhaps to a different extent.

Thus, films of ruthenium and osmium and oxides thereof have suitable properties for a variety of uses in integrated circuits. For example, they can be used in integrated circuits for electrical contacts. They are particularly suitable for use as barrier layers between the dielectric material and the silicon substrate in memory devices, such as ferroelectric memories. Furthermore, they may even be suitable as the plate (i.e., electrode) itself in capacitors.

There are a wide variety of ruthenium and osmium compounds that can be used as precursors for the preparation of such films. Many are particularly well suited for use in chemical vapor deposition techniques. See, for example, U.S. Pat. No. 5,372,849 (McCormick et al.), which discloses the use of ruthenium and osmium compounds containing carbonyl ligands and other ligands. Typically, such compounds can be prepared by the thermal or photolytic reaction of $Ru_3(CO)_{12}$ or $Os_3(CO)_{12}$ with a neutral two electron donor ligand in benzene. See, for example, Johnson et al., *Nature*, 901–902 (1967), and Cowles et al., *Chem. Commun.*, 392 (1969). Although such reactions provide good yields (e.g., 80–90%), they require generally long reaction times (e.g., 4 days). Thus, there is a continuing need for methods for the preparation of such ruthenium and osmium compounds in high yields with shorter reaction times.

SUMMARY OF THE INVENTION

The present invention provides methods for the preparation of compounds of the formula (Formula I):

$$L_yM(CO)_z$$

wherein M is Ru or Os, each L is indepedently a neutral ligand, y=1–4, and z=1–5. These methods involve the reaction of $Ru_3(CO)_{12}$ or $Os_3(CO)_{12}$ with a neutral ligand in a solvent system having a boiling point higher than that of benzene at atmospheric pressure. The solvent system can include one solvent, such as toluene, xylene, substituted benzene, heptane, octane, nonane, or an azeotropic mixture. The azeotropic mixture can contain one or more solvents having a boiling point at atmospheric pressure higher than that of benzene.

Using methods of the present invention, the product yields are preferably higher than conventional methods, and the reaction times are shorter than conventional methods. Preferably, using the methods of the present invention, a complex of Formula I is prepared in greater than about 90% yield, more preferably, in greater than about 95% yield, and most preferably, in greater than about 99% yield. Preferably, using the methods of the present invention, a complex of Formula I is prepared in no greater than about 36 hours, and more preferably, in no greater than about 24 hours.

DETAILED DESCRIPTION OF PREFERRED EMBODIMENTS

The present invention provides methods for the preparation of compounds of the formula (Formula I):

$$L_yM(CO)_z$$

wherein M is Ru or Os, each L is independently a neutral-ligand, y=1–4 (preferably, 1–3, and more preferably, 1), and z=1–5 (preferably, 1–3, and more preferably, 3). These complexes are neutral complexes and may be liquids or solids at room temperature. Typically, they are liquids. If they are solids, they are sufficiently soluble in an organic solvent to allow for vaporization, they can be flash vaporized or sublimed from the solid state, or they have melting temperatures below their decomposition temperatures. Thus, such complexes described herein are suitable for use in chemical vapor deposition (CVD) techniques, such as flash vaporization techniques, bubbler techniques, and/or microdroplet techniques. Preferred embodiments of the complexes described herein are particularly suitable for low temperature CVD techniques.

These methods involve the reaction of $Ru_3(CO)_{12}$ or $Os_3(CO)_{12}$ (referred to herein as "trimer") with a neutral ligand in a solvent system having a boiling point higher than that of benzene at atmospheric pressure. The reaction can occur thermally or photolytically. The solvent system having a boiling point higher than that of benzene at atmospheric pressure can include one solvent or a mixture of solvents that may form an azeotrope, Preferably, the solvent system includes one or more solvents that are less hazardous to an individual than benzene.

The solvents that are suitable for this application can be one or more of the following: saturated or unsaturated hydrocarbons (preferably, $C_6$–$C_{20}$, cyclic, branched, or linear), aromatic hydrocarbons (preferably, $C_6$–$C_{20}$), halogenated hydrocarbons, silylated hydrocarbons such as alkylsilanes, alkylsilicates, ethers, polyethers, thioethers, esters, lactones, amides, amines (aliphatic or aromatic, primary, secondary, or tertiary), polyamines, nitrites, cyanates, isocyanates, thiocyanates, silicone oils, aldehydes, ketones, diketones, carboxylic acids, alcohols, thiols, or compounds containing combinations of any of the above, or mixtures of one or more of the above.

The solvent system preferably includes, for example, toluene, xylene, substituted benzene (e.g., ethylbenzene), heptane, octane, nonane, or mixtures, particularly azeotropic mixtures thereof. The mixtures can contain one or more solvents having a boiling point higher than that of benzene at atmospheric pressure.

The ligands L that are suitable for use in the preparation of compounds of Formula I include neutral ligands. Examples of such ligands include phosphines ($R_3P$), phosphites (($RO)_3P$), amines ($R_3N$), arsines ($R_3As$), stibenes ($R_3Sb$), ethers ($R_2O$), sulfides ($R_2S$), nitriles (RCN), isonitriles (RNC), thiocarbonyls (CS), monoalkenes (linear, branched, or cyclic), dienes (linear, branched, or cyclic), trienes (linear, branched, or cyclic), bicyclic alkenes, bicyclic dienes, bicyclic trienes, tricyclic alkenes, tricyclic dienes, tricyclic trienes, and alkynes. Although the structures for each of the unsaturated ligands (monoalkenes, dienes, trienes, alkynes, etc.) are not shown, they would also include R groups attached to the main carbon chain. The R groups can be hydrogen, a halide (particularly fluorine), or an organic group, which may be substituted or unsubstituted. The organic R groups preferably include about 1 to about 8 carbon atoms, and more preferably, about 1 to about 2 carbon atoms. The unsaturated ligands preferably include about 4 to about 8 carbon atoms, and more preferably, about 6 to about 8 carbon atoms. Preferably, the neutral ligands are selected from the group of linear, branched, or cyclic dienes, bicyclic dienes, tricyclic dienes, and combinations thereof.

As used herein, the term "organic group" means a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). In the context of the present invention, the organic groups are those that do not interfere with the formation of compounds of Formula I. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Substitution is anticipated on the organic groups of the complexes of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

Complexes of Formula I are disclosed, for example in U.S. Pat. No. 5,372,849 (McCormick et al.) and Applicants' Assignees' copending patent application entitled "Precursor Chemistries for Chemical Vapor Deposition of Ruthenium and Ruthenium Oxide" having Ser. No. 09/141,236 filed Aug. 27, 1998. A preferred class of complexes formed by the methods of the present invention include (cyclohexadienyl) $Ru(CO)_3$ and (cycloheptadienyl)$Ru(CO)_3$. These complexes are particularly advantageous because they are volatile liquids.

The methods of the present invention include using the ligand L in an excess amount (e.g., up to about a 20-fold excess, and preferably, about 3-fold to about 10-fold excess) relative to the ruthenium or osmium trimer, optionally in the presence of CO, at a temperature at which the solvent system refluxes. The total amount of ligand L can be added to the trimer initially, or it can be added in portions throughout the reaction. Alternatively, the total amount of trimer or portions thereof may be added to ligand L. The reaction can be carried out in air, however, it is preferably carried out in an inert atmosphere (e.g., nitrogen or argon) using refluxing apparatus.

Significantly, using a solvent or mixture of solvents having a boiling point greater than that of benzene at atmospheric pressure produces a complex of Formula I in relatively high yields (preferably, greater than about 90% yield, more preferably, greater than about 95%, and most preferably, greater than about 99%) in a relatively short period of time (preferably, in no greater than about 36 hours, and more preferably, in no greater than about 24 hours). Compared to the same reaction in benzene, the present invention can provide significantly shorter reaction times and higher yields.

The product can be isolated from the reaction mixture in a variety of ways. Typically, it is isolated by removing the solvent(s) and unreacted ligand in vacuo, with optional heating of the reaction mixture. Significantly, once removed from the product, the solvent(s) and unreacted ligand can be reused by adding trimer in the desired amount.

The following examples are offered to further illustrate the various specific and preferred embodiments and techniques. It should be understood, however, that many variations and modifications may be made while remaining within the scope of the present invention.

EXAMPLES

All experiments were carried out under argon using standard inert gas techniques. FTIR spectra were run on a Nicolet Magna-IR 550 Spectrometer. Mass spectra were collected on a Varian Saturn II instrument. NMR spectra were obtained at Spectral Data Services, Champaign, Ill.

Preparation of Tricarbonyl(1,3-cylohexadiene) ruthenium

Under an atmosphere of dry argon, toluene (30 mL) and 1,3-cyclohexadiene (22.3 mL, 18.75 g, 234 mmol) were added to triruthenium dodecacarbonyl (10 g, 15.6 mmol). The red colored reaction mixture was heated to reflux. After 24 hours, the solution had a red/yellow color and the reflux was stopped. The solvent and the unreacted ligand were removed in vacuo. Vacuum distillation of the remaining solution yielded tricarbonyl(1,3-cyclohexadiene)ruthenium (12 g, 45.2 mmol) as a light yellow liquid that was collected at approximately 35° C. and 50 mTorr. Yield: 96.6%. FTIR (in Nujol): 2061, 2986, 1953, 1181, 585, 558, 529, 504 cm$^{-1}$. $^1$H NMR (in C$_6$D$_6$): δ 4.8 dd, 2.8 m, 1.4 m. $^{13}$C[$^1$H] NMR (in C$_6$D$_6$): δ 199 s, 87 d, 56 d, 25 t. Mass spec: m/e 236, 208, 153, 130, 102, 78, 63, 39.

For comparison purposes, see Applicants' Assignees' copending patent application entitled "Precursor Chemistries for Chemical Vapor Deposition of Ruthenium nad Ruthenium Oxide" having Ser. No. 09/141,236 filed Aug. 27, 1998. Therein, the above complex was synthesized in refluxing benzene, producing a yield of about 70% and requiring a reaction time of about 5 days.

Preparation of Tricarbonyl(1,3-cycloheptadiene) ruthenium

Under an atmosphere of dry argon, toluene (20 mL) and 1,3-cycloheptadiene (2.0 mL, 1.74 g, 18.4 mmol) are added to triruthenium dodecacarbonyl (1.0 g, 1.56 mmol). The red colored reaction mixture is heated to reflux. After 24 hours, the solution has a red/yellow color and the reflux was stopped. The solvent and the unreacted ligand were removed in vacuo. Vacuum distillation of the remaining solution yields tricarbonyl(1,3-cycloheptadiene)ruthenium as a light yellow liquid that is collected at approximately 50° C. and 70 mTorr. FTIR (in Nujol): 3038, 2981, 2060, 1995, 1970, 1055, 580, 560, 525 cm$^{-1}$. $^1$H NMR (in C$_6$D$_6$): δ 4.8 dd, 2.7 m, 1.65 m, 1.15 m. $^{13}$C[$^1$H] NMR (in C$_6$D$_6$): δ 90 d, 54 d, 28 t., 27.5 t.

All patents, patent applications, and publications are herein incorporated by reference in their entirety, as if each were individually incorporated. The foregoing detailed description and examples have been given for clarity of understanding only. No unnecessary limitations are to be understood therefrom.

The invention is not limited to the exact details shown and described, for variations obvious to one skilled in the art will be included within the invention defined by the claims.

What is claimed is:

1. A method for the preparation of a compound of Formula I:

$$L_yM(CO)_z$$

wherein M is Ru or Os, each L is independently a neutral ligand, y=1–4, and z=1–5, the method comprising reacting Ru$_3$(CO)$_{12}$ or Os$_3$(CO)$_{12}$ in an inert atmosphere with a neutral ligand in a solvent system having a boiling point higher than that of benzene at atmospheric pressure and wherein the solvent system comprises two or more solvents.

2. The method of claim 1 wherein the inert atmosphere is selected from the group consisting of nitrogen and argon.

3. The method of claim 1 wherein the solvent system comprises a solvent selected from the group of saturated or unsaturated hydrocarbons, aromatic hydrocarbons, halogenated hydrocarbons, silylated hydrocarbons, ethers, polyethers, thioethers, esters, lactones, amides, amines, polyamines, nitrites, cyanates, isocyanates, thiocyanates, silicone oils, aldehydes, ketones, diketones, carboxylic acids, alcohols, thiols, and mixtures of one or more of the above.

4. The method of claim 3 wherein the solvent system comprises at least one solvent selected from the group of toluene, xylene, substituted benzene, heptane, octane, nonane, and combinations thereof.

5. The method of claim 1 wherein a complex of Formula I is prepared in an amount of greater than about 90%.

6. The method of claim 5 wherein a complex of Formula I is prepared in an amount of greater than about 95%.

7. The method of claim 6 wherein a complex of Formula I is prepared in an amount of greater than about 99%.

8. The method of claim 1 wherein a complex of Formula I is prepared in an amount of greater than about 90% in no greater than about 36 hours.

9. The method of claim 8 wherein a complex of Formula I is prepared in an amount of greater than about 90% in no greater than about 24 hours.

10. The method of claim 1 wherein each L is independently selected from the group of phosphines, phosphites, amines, arsines, stibenes, ethers, sulfides, alkylidenes, nitriles, isonitriles, thiocarbonyls, linear, branched, or cyclic monoalkenes, linear, branched, or cyclic dienes, linear, branched, or cyclic trienes, bicyclic alkenes, bicyclic dienes, bicyclic trienes, tricyclic alkenes, tricyclic dienes, tricyclic trienes, and alkynes.

11. The method of claim 10 wherein L is selected from the group of linear, branched, or cyclic dienes, bicyclic dienes, tricyclic dienes, and combinations thereof.

12. A method for the preparation of a compound of Formula I:

$$L_yM(CO)_z$$

wherein M is Ru or Os, each L is independently a neutral ligand, y=1–4, and z=1–5, the method comprising reacting Ru$_3$(CO)$_{12}$ or Os$_3$(CO)$_{12}$ with a neutral ligand in a solvent system having a boiling point higher than that of benzene at atmospheric pressure and wherein the solvent system comprises two or more solvents, wherein the neutral ligand is present in an amount of up to about a 20-fold excess relative to Ru$_3$(CO)$_{12}$ or Os$_3$(CO)$_{12}$.

13. The method of claim 12 wherein the neutral ligand is present in an amount of about a 3-fold excess to about a 10-fold excess relative to Ru$_3$(CO)$_{12}$ or Os$_3$(CO)$_{12}$.

14. The method of claim 12 wherein the solvent system comprises a solvent selected from the group of saturated or unsaturated hydrocarbons, aromatic hydrocarbons, halogenated hydrocarbons, silylated hydrocarbons, ethers, polyethers, thioethers, esters, lactones, amides, amines, polyamines, nitrites, cyanates, isocyanates, thiocyanates, silicone oils, aldehydes, ketones, diketones, carboxylic acids, alcohols, thiols, and mixtures of one or more of the above.

15. The method of claim 14 wherein the solvent system comprises at least one solvent selected from the group of toluene, xylene, substituted benzene, heptane, octane, nonane, and combinations thereof.

16. The method of claim 12 wherein a complex of Formula I is prepared in an amount of greater than about 90%.

17. A method for the preparation of a compound of Formula I:

$$L_yM(CO)_z$$

wherein M is Ru or Os, each L is independently a neutral ligand, y=1–4, and z=1–5, the method comprising reacting Ru$_3$(CO)$_{12}$ or Os$_3$(CO)$_{12}$ in the presence of CO with a neutral ligand in a solvent system having a boiling point higher than that of benzene at atmospheric pressure and wherein the solvent system comprises two or more solvents, wherein the neutral ligand is present in an amount of up to about a 20-fold excess relative to Ru$_3$(CO)$_{12}$ or Os$_3$(CO)$_{12}$.

18. The method of claim 17 wherein the neutral ligand is present in an amount of about a 3-fold excess to about a 10-fold excess relative to Ru$_3$(CO)$_{12}$ or Os$_3$(CO)$_{12}$.

19. The method of claim 17 wherein the solvent system comprises a solvent selected from the group of saturated or unsaturated hydrocarbons, aromatic hydrocarbons, halogenated hydrocarbons, silylated hydrocarbons, ethers, polyethers, thioethers, esters, lactones, amides, amines, polyamines, nitrites, cyanates, isocyanates, thiocyanates, silicone oils, aldehydes, ketones, diketones, carboxylic acids, alcohols, thiols, and mixtures of one or more of the above.

20. The method of claim 19 wherein the solvent system comprises at least one solvent selected from the group of toluene, xylene, substituted benzene, heptane, octane, nonane, and combinations thereof.

* * * * *

UNITED STATES PATENT AND TRADEMARK OFFICE
CERTIFICATE OF CORRECTION

PATENT NO. : 6,114,557  
DATED : September 5, 2000  
INVENTOR(S) : Uhlenbrock et al.

Page 1 of 1

It is certified that error appears in the above-identified patent and that said Letters Patent is hereby corrected as shown below:

Column 5,  
Line 56, after "polyamines," delete "nitrites" and insert therefor -- nitriles --.

Column 6,  
Line 40, after "polyamines," delete "nitrites" and insert therefor -- nitriles --.

Column 7,  
Line 4, after "polyamines," delete "nitrites" and insert therefor -- nitriles --.

Signed and Sealed this

Twentieth Day of November, 2001

Attest:

*Nicholas P. Godici*

NICHOLAS P. GODICI  
*Acting Director of the United States Patent and Trademark Office*

*Attesting Officer*